US006803477B2

(12) United States Patent
Prakash et al.

(10) Patent No.: US 6,803,477 B2
(45) Date of Patent: Oct. 12, 2004

(54) MAGNESIUM MEDIATED PREPARATION OF FLUORINATED ALKYL SILANES

(75) Inventors: G. K. Surya Prakash, Hacienda Heights, CA (US); Jinbo Hu, Los Angeles, CA (US); George A. Olah, Beverly Hills, CA (US)

(73) Assignee: University of Southern California, Los Angeles, CA (US)

( * ) Notice: Subject to any disclaimer, the term of this patent is extended or adjusted under 35 U.S.C. 154(b) by 84 days.

(21) Appl. No.: 10/305,025

(22) Filed: Nov. 27, 2002

(65) Prior Publication Data

US 2003/0153778 A1 Aug. 14, 2003

Related U.S. Application Data

(60) Provisional application No. 60/334,361, filed on Nov. 29, 2001.

(51) Int. Cl.$^7$ .................................................. C07F 7/04
(52) U.S. Cl. ...................... 556/478; 556/476; 556/488
(58) Field of Search ............................... 556/478, 476, 556/488

(56) References Cited

U.S. PATENT DOCUMENTS

| 4,968,848 A | 11/1990 | Kruse et al. ................. 568/812 |
| 5,446,218 A | 8/1995 | Webster et al. .............. 570/169 |
| 6,203,721 B1 | 3/2001 | Roques et al. ......... 252/183.13 |
| 6,355,849 B1 | 3/2002 | Roques et al. .............. 570/144 |

FOREIGN PATENT DOCUMENTS

| EP | 0 733 614 A1 | 9/1996 |
| WO | WO 9822435 | 5/1998 |

OTHER PUBLICATIONS

G.K. Surya Prakash, et al.; "Perfluoroalkylation with Organosilicon Reagents";Chemical Reviews, Reprinted form vol. 97, No. 5, pp. 757–786 (1997).

G.K. Surya Prakash, et al.; "Fluoride–Induced Trifluoromethylation of Carbonyl Compounds with Trifluoromethyltrimethylsilane (TMS–CF$_3$)"; J. Am. Chem. Soc., 111, 393–395 (1989).

Ingo Ruppert et al.; "Die Ersten CF$_3$–Substituierten Organyl (Chlor) Silane"; Tetrahedron Letters, vol. 25, No. 21, pp. 2194–2198, (1984).

Jack Hine, et al.; The Formation of Difluoromethylene from Difluoromethyl Phenyl Sulfone and Sodium Methoxide; The School of Chemistry of the Georgia Institute of Technology, Atlanta 23, GA, Journal of Am. Chem. Soc.; vol. 82; pp 82, 6178; (1960).

Jack Hine, et al.; "Methylene Derivatives as Intermediates in Polar Reactions. VIII. Difluoromethylene in the Reaction of Chlorodifluoromethane with Sodium Methoxide" The School of Chemistry of the Georgia Institute of Technology, Journal of Am. Chem. Soc.; pp. 79, 3493 (1957).

G. Patrick Stahly; "Nucleophilic Addition of Difluoromethyl Phenyl Sulfone to Aldehydes and Various Transformations of the Resulting Alcohols";Journal of Fluorine Chemistry, vol. 43; pp. 53–56; (1969).

Donald J. Burton; "Synthesis of Bromodifluoromethyl Phenyl Sulfide, Sulfoxide and Sulfone [1]" Journal of Fluorine Chemistry, vol. 18 pp. 573–582 (1981).

Takeshi Nakai, et al.; "The Reaction of 2,2,2–Trifluoroethyl Iodide with Sodium Phenolate. A Novel Competition Between Substitution and Elimination Reactions"; Journal of Fluorine Chemistry, vol. 9; pp. 89–93 (1977).

Jack Hine, et al,; "The S$_n$2 Reactivity of β Fluoroethyl Iodides" JOC, vol. 23, pp. 23,1550 (1958).

Abstract: Xingya, Li; "Halophilic reactions to nucleophiles. 2. crown ether–promoted reactions of dibromodifluoromethane and sodium thiophenoxide"; SciFinder Scholar, Nov. 6, 2002, pp. 2.

Zheng–Yu Long, et al.; S$_{rn}$1 reactions of 2,2,2–trifluoroethyl halides with thiolate ions Journal of Fluorine Chemistry, vol. 91 pp. 95–98 (1998).

Toshiki Hagiwara, et al.; "Difluoroalkylation of Carbonyl Compounds with (1.1 Difluoroalkyl) silane derivatives" Sagami Chemical Research Center, Nashi–Chnuma 4.4.1 Sagmihara, Kanagawa 229, Japan, SYNLETT(1995).

S.G. Surya Prakash; "Fluoride–Induced Trifluoromethylation of Carbonyl Compounds with Trifluoromethylrimethylsilane (TMS–CF$_3$) A Trifluoromethide Equivalent";J. Am. Chem. Soc. vol. 111, pp, 393–395, 1989.

Ingo Ruppert; "Die Ersten CF$_3$–Substituierten organyl (Chlor) Silane"; Tetrahedron Letters, vol. 25, No. 21, pp. 2195–2198, (1984).

S. Sibille, et al.; "Electrochemical Trifluoromethylation of Carbonyl Compounds", Tetrahedron Letters, vol. 45, No. 5, pp. 1423–1428 (1989).

Samia Ait–Mohand, et al.; "Nucleophilic Trifluoromethylation Using Trifluoromethyl Iodide. A New and Simple Alternative for the Trifluoromethylation of Aldehydes and Ketones",Organic Letters, vol. 3, No. 26, 4271–7273. (2001).

(List continued on next page.)

*Primary Examiner*—Samuel Barts
(74) *Attorney, Agent, or Firm*—Winston & Strawn LLP

(57) ABSTRACT

An efficient method is disclosed for the preparation of trifluoromethyl- and difluoromethylsilanes using magnesium metal mediated reductive tri- and difluoromethylation of chlorosilanes with tri- and difluoromethyl sulfides, sulfoxides, and sulfones. One byproduct of the process is diphenyl disulfide. Since phenyl trifluoromethyl sulfone, sulfoxide and sulfide are readily prepared from readily available trifluoromethane and diphenyl disulfide, the method can be considered "pseudo-catalytic" for the preparation of (trifluoromethyl)trimethylsilane from environmentally benign trifluoromethane.

14 Claims, 5 Drawing Sheets

OTHER PUBLICATIONS

William B. Motherwell, et al.; "The Trifluoromethylacetophenone, N, N–dimethyltrimethysilylamine Adduct—A New Shelf Stable Reagent for Nucleophilic Trifluoromethylation"; Synlett 2002, No. 4, vol. 29, 03, ISSN 0936–5214, p. 646 (2002).

Tatsuya Shono, et al.; "Electrooganic Chemistry. 130. A novel Trifluoromethylation Aldehydes and Ketones Promoted by an Electrogenerated Base", J. Org. Chem, vol. 56, pp. –2–4 (1991).

Rachid Barhadidi, et al.; "Coupling of fluoroform with aldehydes using an electrogenerated base"; Chem. Commun, p. 1251 (1998).

Benoit Folleas, et al.; "Fluoroform: an efficient precursor for the trifluoromethylation of aldehydes"; Tetrahedron Letters 39, pp. 2973–2976 (1998).

Benoit Folleas, et al.; "Fluoroform: an efficient precursor for the trifluoromethylation of aldehydes", Tetrahedron Letters 56, 275–283 (2000).

Jamie Russell, et al.; "Effective Nucleophilic Trifluoromethylation with Fluoroform and Common Base",Tetrahedron 54, pp. 13771–13782 (1998).

Sylvie Large, et al.; "Nucleophilic Trifluoromethylation of Carbonyl Compounds and Disulfides with Trifluoromethane and Silicon–containing Bases", J. Orig. Chem., vol. 65, pp. 8848–8856, (2000).

Clotilde Mispelaere, et al.; Hemiaminals of Trifluoroacetaldehyde, as Trifluoromethylating Agents Tetrahedron Letters 40, pp. 6411–6414 (1999).

T. Billard, et al.; "New Stable Reagents for the Nucleophilic Trifluoromethylation. 1. Trifluoromethylation of Carbonyl Compounds with N–Formylmorpholine Derivatives" 2000 American Chemical Society; Organic Letters, vol. 2, pp. 2101–2102 (2000).

Thierry Billard, et al.; "Trifluoromethylation of Nonenolizable Carbonyl Compounds with a Stable Piperazino Hemiaminal of Trifluoroacetaldehyde", Eur. J. Org. Chem. pp. 1467–1471 (2001).

Thierry Billard, et al.; "Reactivity of Stable Trifluoroacetaldehyde Hemiaminals. 2. Generation and Synthetic Potentialities of Fluorinated Iminiums", J. Org. Chem., vol. 67. pp. 997–1000 (2002).

Ingo Ruppert, et al., "Die Ersten $CF_3$—Substituierten Organyl (Chlor) Silane", Tetrahedron Letters, vol. 25, No. 21, pp. 2195–2198, (1984).

G. Pawelke; "Tetrakis (Dimethylamino) Ethylene/Trifluoroiodomethane, a Specifc Novel Trifluoromethylating Agent", Journal of Fluorine Chemistry, vol. 42 . pp. 429–433 (1989).

Ramesh Krishnamurti, et al.; "Preparation of Trifluoromethyl and Other Perfluoroalkyl Compounds with (Perfluroalkyl) trimethysilanes", J. Org. Chem., vol. 56, pp. 984–989 (1991).

Pichika Ramaiah, et al.; "1–Trifluormethyl–1–Cyclohexanol (Cyclohexanol, 1–(trifluoromethyl)–)", Organic Syntheses, vol. 72, pp. 232–241 (1995).

G.K. Suyra Prakash, et al.; "Convenient and Safe Electrochemical Synthesis of (Trifluoromethyl) trimethylsilane[1a]" Synlett, pp. 1057 (1994).

Frederic Aymard, et al.; "An Efficient Inexpensive Electrochemical Preparation of Ruppert's Reagent", Tetrahaedron Letters, vol. 35, No. 46, pp. 8623–8624, (1994).

Joseph Grobe, et al.; "Facile Aluminum Induced Synthesis of (Trifluoromethyl) trimethysilane", Synlett, p. 641 (1995).

Kenji Uneyama, et al.; "A review of Mg metal–promoted C–F bond activation; a reliable synthetic approach to difluorinated organic compounds" Journal of Fluorine Chemistry, vol. 114, pp. 127–131 (2002).

G.K. Surya Prakash, et al.; "Facile preparation of di–and monofluoromethyl ketones from trifluoromethyl ketones via fluorinated enol silyl ethers", Journal of Fluorine Chemistry, vol. 112 pp. 357–362 (2001).

Ikuzo Nishiguchi, et al.; "Facile O–Silylation of Tertiary Alcohols in the Presence of Mg Metal", Synlett No. 7, pp. 1025–1027, (2000).

Yoshio Ishino, et al.; "Mg–Promoted Reductive Cross Coupling of Carbonyl Compounds with Trimethylsilyl Chloride", Chemistry Letters, p. 829 (1995).

Toshinobu Ohno, et al.; "Mg–Promoted Regio–and Stereoselective C–Acylation of Aromatic a, β–Unsaturated Carbonyl Compounds", Organic Letters, vol. 3, No. 22, pp. 3439–3442 (1995).

(I)

(II)

(X = F, H)

US 6,803,477 B2

MAGNESIUM MEDIATED PREPARATION OF FLUORINATED ALKYL SILANES

CROSS-REFERENCE TO RELATED APPLICATIONS

This application claims the benefit of provisional application No. 60/334,361 filed Nov. 29, 2001.

TECHNICAL FIELD

This invention relates to a process of preparation of fluorinated alkyl silanes such as trifluoromethyl- and difluoromethylsilanes, as well as to the reactants used in this process. The invention more particularly relates to a technique for tri- and difluoromethylation typically carried out with tri- and difluoromethyl organosulfur compounds and a reducing metal such as magnesium.

BACKGROUND ART

The introduction of the trifluoromethyl ($CF_3$) and the difluoromethyl ($CF_2H$) groups into organic molecules has gained increasing attention due to the potential use of trifluoromethylated and difluoromethylated compounds in materials science, medicinal and agrochemistry. Although there are few approaches to achieve this goal, the fluoride induced trifluoromethylation or difluoromethylation with organosilicon reagents ($R_fSiR_3$, $R_f=CF_3$, $CF_2H$) has been considered a straightforward and reliable method. (Trifluoromethyl)trimethylsilane (TMS-$CF_3$), first developed by Prakash, G. K. S.; Krishnamuti, R.; Olah, G. A. in 1989 (*J. Am. Chem. Soc.* 1989, 111, 393), as a nucleophilic trifluoromethylating reagent of choice under mild conditions, is widely used and also works with enolizable carbonyl compounds. Although several other types of nucleophilic trifluoromethylation methods have been appeared in literature thereafter, such as (1) direct introduction of trifluoromethyl group by electroreduction of bromotrifluoromethane into carbonyl-containing molecules: Sibille, S.; Mcharek, S.; Perichon, J. *Tetrahedron* 1989, 45, 1423; (2) using $CF_3I$ as a trifluoromethylating reagent: Ait-Mohand, S.; Takechi, N.; Medebielle, M.; Dolbier, W. Jr. *Org. Lett.* 2001, 3, 4271; (3) using trifluoromethylacetophenone-N,N-dimethyltrimethylsilylamine adduct as a trifluoromethylating agent: Motherwell, W. B.; Storey, L. *Synlett* 2002, 646; (4) using trifluoromethane as a trifluoromethylating precursor: (a) Shono, T.; Ishifume, M.; Okada, T.; Kashimura, S. *J. Org. Chem.* 1991, 56, 2. (b) Barhdadi, R.; Troupel, M.; Perichon, *J. Chem. Comm.* 1998, 1251. (c) Folleas, B.; Marek, I.; Normant, J.-F.; Saint-Jalmes, L. *Tetrahedron Lett.* 1998, 39, 2973. (d) Folleas, B.; Marek, I.; Normant, J.-F.; Saint-Jalmes, L. *Tetrahedron* 2000, 56, 275. (e) Russell, J.; Roques, N. *Tetrahedron* 1998, 54, 13771. (f) Large, S.; Roques, N.; Langlois, B. R. *J. Org. Chem.* 2000, 65, 8848. (g) Roques, N.; Russell, J.; Langlois, B.; Saint-Jalmes, L.; Large, S *PCT Int. Appl.* 1998, WO 9822435. (h) Roques, N.; Mispelaere, *Tetrahedron Lett.* 1999, 6411; (5) using $CF_3^-$/N-formylmorpholine adduct as a trifluoromethylating agent: Billard, T. B.; Langlois, B. R. *Org. Lett.* 2000, 2, 2101; (6) using piperazino hemiaminal of trifluoroacetaldehyde as a trifluoromethylating agent: (a) Billard, T.; Langlois, B. R.; Blond, G. *Eur. J. Org. Chem.* 2001, 1467. (b) Billard, T.; Langlois, B. R. *J. Org. Chem.* 2002, 67, 997. However, all these recently developed methods are inefficient in the case of enolizable systems.

TMS-$CF_3$ was first prepared by Ruppert et al. and published in *Tetrahedron Lett.* 1984, 25, 2195. Since then several other procedures have been developed via both chemical and electrochemical methods during last two decades: (a) In 1989 Pawelke reported a preparative route to TMS-$CF_3$ using chlorotrimethylsilane (TMSCl), trifluoromethyl iodide and tetrakis(dimethylamino)ethylene: Pawelke, G. *J. Fluorine Chem.* 1989, 42, 429. (b) In 1991 Prakash et al. published a modified Ruppert procedure to prepare TMS-$CF_3$: Krishnamurti, R.; Bellew D. R.; Prakash G. K. S. *J. Org. Chem.* 1991, 56, 984; Ramaiah, P.; Krishnamurti, R.; Prakash, G. K. S. *Org. Syn.* 1995, 72, 232. (c) In 1994 Prakash et al. developed a new and efficient electrochemical trimethylsilylation of bromotrifluoromethane to produce TMS-$CF_3$: Prakash, G. K. S.; Deffieux, D.; Yudin, A. K.; Olah, G. A. *Synlett* 1994, 1057. (d) In 1994 Nedelec et al. reported an electrochemical reduction of $CF_3Br$ in N,N-dimethylformamide (DMF) in the presence of TMSCl and a sacrificial aluminum anode to produce TMS-$CF_3$: Aymard, F.; Nedelec, J.-Y.; Perichon, J. *Tetrahedron Lett.* 1994, 35, 8623. (e) In 1995, Grobe and Hegge reported trifluoromethylation of TMSCl with bromotrifluoromethane and aluminum metal in N-methylpyrrolidinone (NMP) to produce TMS-$CF_3$: Grobe, J.; Hegge, J. *Synlett* 1995, 641.

However, all of these methods have some drawbacks. First of all they all use bromotrifluoromethane ($CF_3Br$) or iodotrifluoromethane ($CF_3I$) as a source for the trifluoromethyl group. Trifluoromethyl halides, particularly $CF_3Br$, in general are ozone depleting and recently their manufacture and use are regulated. Second, these procedures need special apparatus and well-controlled reaction conditions, and the product yields vary widely. Finally, none of the reported methods are amenable for the preparation of structurally diverse trifluoromethylsilanes. Compared with the trifluoromethylation, little is known on the nucleophilic difluoromethylation: Hagiwara, T.; Fuchikami, T. *Synlett* 1995, 717. This is mainly due to the lack of general and efficient methods for the preparation of difluoromethylsilanes. There is an evident need for a new general, economic and efficient method for the preparation of structurally diverse trifluoromethyl- and difluoromethylsilanes.

Magnesium metal promoted reactions through electron transfer process have attracted increasing interest recently, such as C-F bond cleavage of trifluoromethyl ketones, trifluoroacetates, trifluoromethylimines, p-bis(trifluoromethyl)benzene and difluoromethyl ketones, O-silylation of tertiary alcohols, cross coupling of carbonyl compounds with TMSCl, and C-acylation of aromatic α,β-unsaturated carbonyl compounds. (a) Uneyama, K.; Amii H. *J. Fluorine Chem.* 2002, 114, 127. (b) Prakash, G. K. S.; Hu, J.; Olah, G. A. *J. Fluorine Chem.* 2001, 112, 357–362. (c) Nishigachi, I.; Kita, Y.; Watanabe, M.; Ishino, Y.; Ohno, T.; Maekawa, H. *Synlett* 2000, 1025. (d) Ishino, Y.; Maekawa, H.; Takenchi, H.; Sukata, K.; Nishiguchi, I. *Chem. Lett.* 1995, 829. (e) Ohno, T.; Sakai, M.; Ishino, Y.; Shibata, T.; Maekawa, H.; Nishiguchi, I. *Org. Lett.* 2001, 3, 3439. However, the magnesium metal mediated reductions of trifluoromethyl and difluoromethyl sulfones or sulfoxides are still not explored.

In the trifluoromethyl and difluoromethyl sulfones or sulfoxides, due to the strong electron withdrawing effect of $CF_3$ and $CF_2H$ groups, the bond between the pseudohalide and the sulfur atom is sufficiently polarized with the pseudohalide group bearing substantial negative charge. Thus, when the electrons are transferred from magnesium metal to the sulfones and sulfoxides, reductive cleavage of the C—S bond to generate anionic $CF_3^-$ or $CF_2H^-$ species was anticipated over the C—F bond fission. These reactions are shown in FIG. 1 as schemes I and II.

Moreover, phenyl trifluoromethyl sulfone (1) or phenyl trifluoromethyl sulfoxide (2) can also be conveniently prepared from environmentally benign precursors by the schemes illustrated in FIG. 2. Precursors such as trifluoromethane ($CF_3H$) or trifluoroacetate (see FIG. 2, scheme I), while difluoromethyl phenyl sulfone (4) can be obtained using known methods (see FIG. 2, scheme II). (a) Roques, N.; Russell, J.; Langlois B.; Saint-Jalmes, L.; Large S. U.S. Pat. No. 6,203,721 B1 (2001); PCT application: WO98/22435 (1998). (b) Gerard, F.; Jean-Mannel, M.; Laurent, S.-J. Eur. Pat. Appl. 1996, EP 733614. (c) Hine, J.; Porter, J. J. Am. Chem. Soc. 1960, 82, 6178.

With these considerations in mind, a magnesium mediated reductive fluoroalkylation of chlorosilanes has been developed, thus providing a long sought after yet simple and efficient method for preparing various fluorinated alkyl silanes.

SUMMARY OF THE INVENTION

Accordingly, this invention provides a method for preparing fluorinated alkyl silanes by reacting a fluorinated alkyl sulfur containing compound, such as a fluorinated alkyl sulfone, a fluorinated alkyl sulfoxide or a fluorinated alkyl sulfide, with a silyl chloride in the presence of a reducing agent under reaction conditions sufficient to prepare a fluorinated alkyl silane. The reaction conditions include a temperature of between −50 and 30° C. and for a time of between 10 minutes and 24 hours, and preferably include a temperature of between −40 and 20° C. and for a time of between 20 minutes and 6 hours. The reaction is advantageously conducted in the presence of a reducing agent that is preferably a metal such as magnesium or zinc. The reaction is preferably carried in the presence of a solvent.

Another aspect of the invention is the provision of an autocatalytic method for the preparation of these fluorinated alkyl silanes. When the fluorinated alkyl sulfur containing reactant is phenyl trifluoromethyl sulfide, it can be prepared from the reaction of trifluoromethane and diphenyl disulfide. The subsequent reaction that forms the fluorinated alkyl silane product generates diphenyl disulfide, which then can react with trifluoromethane to provide further reactants.

The resulting fluorinated alkyl silane product may be subsequently used as a nucleophilic fluoromethylating agent.

BRIEF DESCRIPTION OF THE DRAWING FIGURES

The invention can be better understood with reference to the appended drawing figures, wherein.

DETAILED DESCRIPTION OF THE PREFERRED EMBODIMENTS

In the present method, fluorinated alkyl silanes are prepared by reacting a fluorinated alkyl sulfur containing compound with a silyl chloride in the presence of a reducing agent under reaction conditions sufficient to prepare a fluorinated alkyl silane.

The preferred fluorinated alkyl sulfur containing compound is a fluorinated alkyl sulfone, a fluorinated alkyl sulfoxide or a fluorinated alkyl sulfide, and the method is preferably conducted as follows:

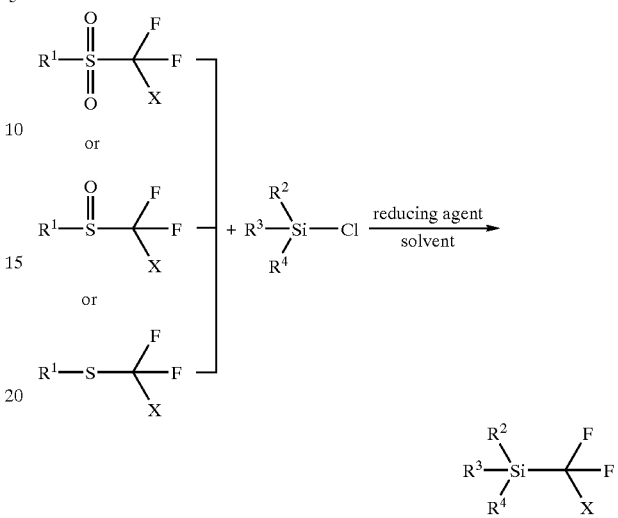

($X = F$ or $H$; $R^1$ = aryl, alkyl; $R^2, R^3, R^4$ = acyclic, cyclic, alkyl or aryl; solvent = DMF, THF, DMSO, etc.)

Advantageously, $R^1$ is an alkyl group of between 1 and 24 and preferably 1 and 12 carbon atoms that is linear or branched or cyclic, in single or fused rings, and is optionally substituted with one or more halogen, hydroxy, or alkoxy groups having 1 to eight carbon atoms, wherein the substituent does do not participate in the reaction; or an aryl group of between 6 and 24 preferably 6 and 12 members in a single ring or in fused rings, wherein the members are carbon or hetero atoms of nitrogen, oxygen or sulfur, and the ring(s) are optionally substituted with one to three substituents of an alkyl group having between 1 and 8 carbon atoms, a halogen, an alcohol, or an alkoxide of between 1 and 8 carbon atoms. Also, $R^2$, $R^3$ or $R^4$ independently can be an alkyl group of between 1 and 24 preferably 1 and 12 carbon atoms that are linear or branched or cyclic, in single or fused rings, and is optionally substituted with one or more halogen, hydroxy, or alkoxy groups having 1 to eight carbon atoms, where the substituent does do not participate in the reaction; or an aryl group of between 6 and 24 preferably 6 and 12 carbon atoms in a single ring or in fused rings, optionally substituted with one to three substituents of an alkyl group having between 1 and 8 carbon atoms, a halogen, an alcohol, or an alkoxide of between 1 and 8 carbon atoms. Preferred aryl groups are phenyl groups or heteroaromatic groups such as pyridyl, thiophenyl, furyl, pyrrole and the like.

The reaction conditions can vary over a wide temperature range. Generally, a temperature of between −50 and 30° C. and preferably between 40 and 20° C. can be used. A reaction time of between 10 minutes and 24 hours, and preferably between 20 minutes and 6 hours is suitable.

The reaction is advantageously conducted in the presence of a reducing agent that is preferably a metal. While zinc can be used, magnesium is preferred since it generally provides higher yields. Reducing metals, such as aluminum, indium, sodium or lithium, are not useful and did not work.

The reaction is preferably carried in the presence of a solvent. Preferably, the solvent is an organic solvent such as dimethyl formamide, tetrahydrofuran, dimethyl sulfoxide, dioxane, dimethoxyethane, or tetrahydropyran.

Figure 1:
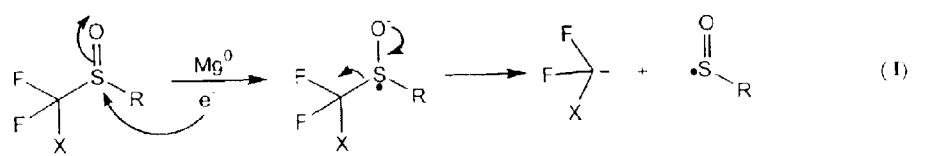
FIG. 1 is an illustration of certain reaction schemes that generate anionic $CF_3^-$ or $CF_2H^-$ species.
Figure 1:
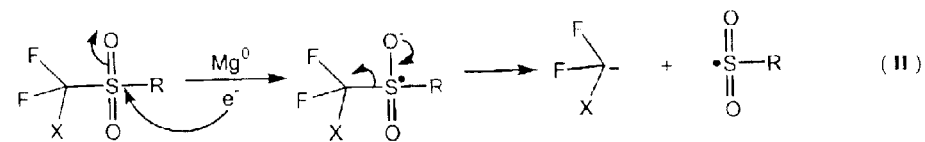
Figure 2:
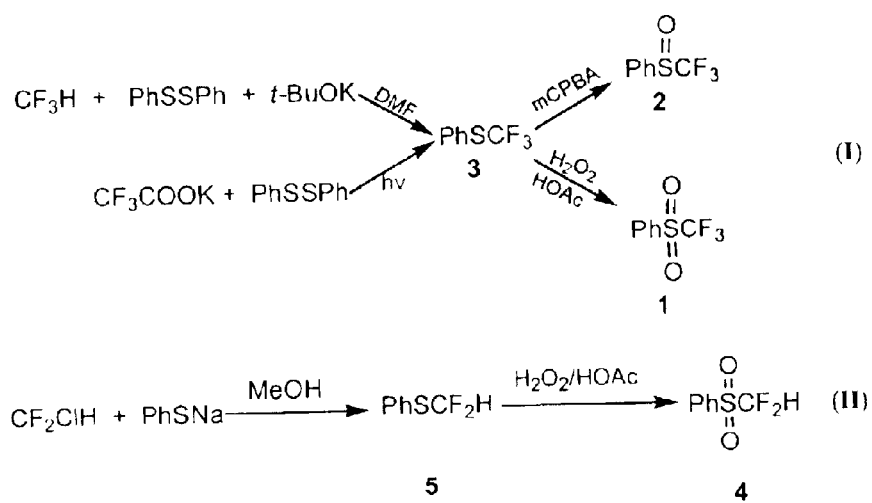
FIG. 2 is an illustration of certain known reaction schemes that generate phenyl trifluoromethyl sulfone or phenyl trifluoromethyl sulfoxide.
Figure 3:
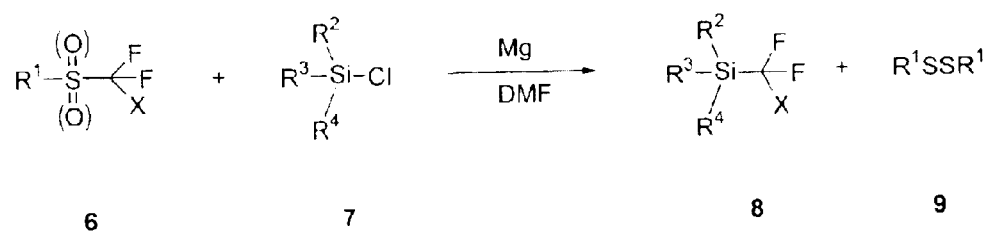
FIGS. 3, 4 and 5 are reaction schemes of the preferred preparation processes of the invention.

The present invention is specifically directed to a general and efficient method for the preparation of trifluoromethyl- and difluoromethyl- silanes via metal mediated reductive tri- and difluoromethylation of chlorosilanes, using trifluoromethyl and difluoromethyl sulfones, sulfoxides or sulfides. A schematic of this method is illustrated in FIG. 3. In this FIG., the starting material can be either a sulfide, sulfone or sulfoxide, where X comprises F or H, $R^1$ comprises aryl and alkyl groups and $R^2$, $R^3$, $R^4$ comprise cyclic or acyclic aryl and alkyl substituents all as defined herein. The experimental examples represent the most preferred embodiments and are listed in TABLE 1.

TABLE 1

Preparation of trifluoromethylsilanes and difluoromethylsilanes through $Mg^0$ mediated reductive cleavage of C-S bond.

| entry | sulfur compound 6 | chlorosilane 7 | temperature[a] | time (h)[b] | product 8 | yields (%)[c] |
|---|---|---|---|---|---|---|
| a | PhSO$_2$CF$_3$ | Me$_3$SiCl | 0° C.~r.t. | 0.5~2 | Me$_3$SiCF$_3$ | 100 (83) |
| b | PhS(O)CF$_3$ | Me$_3$SiCl | 0° C.~r.t. | 0.5~2 | Me$_3$SiCF$_3$ | 100 (81) |
| c | PhSCF$_3$ | Me$_3$SiCl | r.t. | 4 | Me$_3$SiCF$_3$ | 45 |
| d | PhSO$_2$CF$_3$ | Et$_3$SiCl | 0° C.~r.t. | 1.3 | Et$_3$SiCF$_3$ | 100 (95) |
| e | PhS(O)CF$_3$ | Et$_3$SiCl | r.t. | 0.5 | Et$_3$SiCF$_3$ | 98 |
| f | PhSO$_2$CF$_3$ | t-Bu(Me)$_2$SiCl | −30° C.~r.t. | 3 | t-Bu(Me)$_2$SiCF$_3$ | 75 (57) |
| g | PhS(O)CF$_3$ | t-Bu(Me)$_2$SiCl | r.t. | 0.5 | t-Bu(Me)$_2$SiCF$_3$ | 73 |
| h | PhSO$_2$CF$_3$ | (Me$_3$Si)$_3$SiCl | −40° C.~r.t. | 0.5 | (Me$_3$Si)$_3$SiCF$_3$ | 85 (62) |
| i | PhSO$_2$CF$_2$H | Me$_3$SiCl | 0° C. | 1.5 | Me$_3$SiCF$_2$H | 90 (76) |
| j | PhSO$_2$CF$_2$H | Et$_3$SiCl | −40° C.~r.t. | 3 | Et$_3$SiCF$_2$H | 59 (51) |
| k | PhSCF$_2$Br | Me$_3$SiCl | r.t. | 1.0 | PhSCF$_2$Si(CH$_3$)$_3$ | 86 (85) |

TABLE 1-continued

Preparation of trifluoromethylsilanes and difluoromethylsilanes through Mg⁰ mediated reductive cleavage of C-S bond.

| entry | sulfur compound 6 | chlorosilane 7 | temperature[a] | time (h)[b] | product 8 | yields (%)[c] |
|---|---|---|---|---|---|---|
| l | Ph-S(=O)₂-CF₂Br | $Me_3SiCl$ | 0° C.~r.t. | 0.5 | $Me_3SiCF_2CF_2SiMe_3$<br>$Me_3SiCF_2SiMe_3$ | 76 (55)<br>18 |
| m | Ph-S(=O)₂-CF₂SiMe₃ | $Me_3SiCl$ | 0° C.~r.t. | 1.0 | $Me_3SiCF_2CF_2SiMe_3$ | 75 (70) |
| n | (Ph-S(=O)₂-)₂CF₂ | $Me_3SiCl$ | 0° C.~r.t. | 1.0 | $Me_3SiCF_2CF_2SiMe_3$ | 89 (79) |
| o | $H_3C-S(=O)_2-CF_3$ | $Me_3SiCl$ | 0° C.~r.t. | 20 | $Me_3SiCF_3$ | 40 |

[a]The reaction temperature control is critical due to the exothermic nature of the reaction. Larger scale reaction normally needs lower temperature.
[b]The reaction time may vary according to the different reaction scales.
[c]The yields are determined by $^{19}F$ NMR, and the data in parenthese represent isolated yields.

Figure 4:
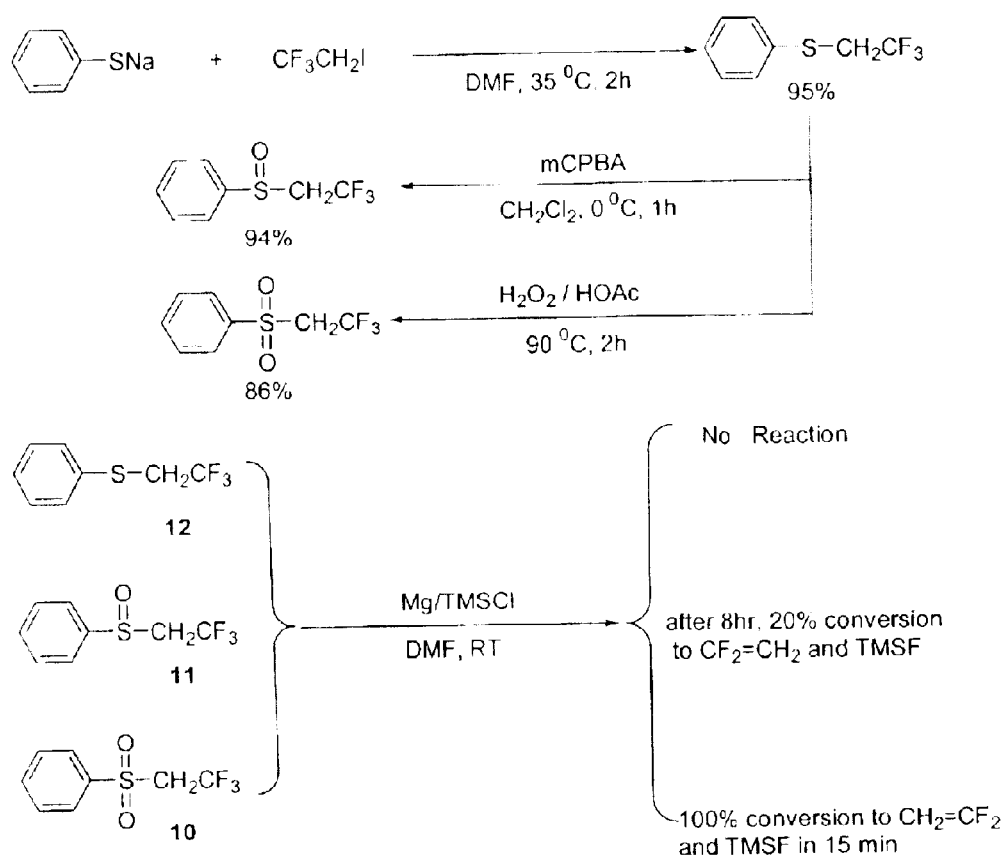

When 2,2,2-trifluoroethyl phenyl sulfone (10) or sulfoxide (11) is reacted with magnesium and TMSCl under the similar reaction conditions, 1,1-difluoroethene was produced readily, as shown by the scheme illustrated in FIG. 4.

Methyl trifluoromethyl sulfone ($CH_3SO_2CF_3$, 13) also reacts with magnesium metal and TMSCl in DMF to produce TMS-CF₃ in moderate yields (40% over a period of 20 hours at room temperature). However, the reaction appears to be sluggish. This indicates that the aromatic ring conjugation in substrate 1 is important to facilitate the initial electron transfer process.

It should also be mentioned that the use of other reducing metals such as zinc are suitable for this type reaction although yield of the products is lower (~30%). Other solvents such as THF can also be used for the reaction, although its use generally requires a prolonged reaction time. This indicates there is no need to invoke $CF_3^-$/DMF adduct as the intermediate for these reactions: Russell J.; Large, S.; Roques, N.; Langlois, B.; Saint-Jalmes, L. WO98/22435; Russell J.; Roques, N. Tetrahedron 1998, 13771.

Figure 5:
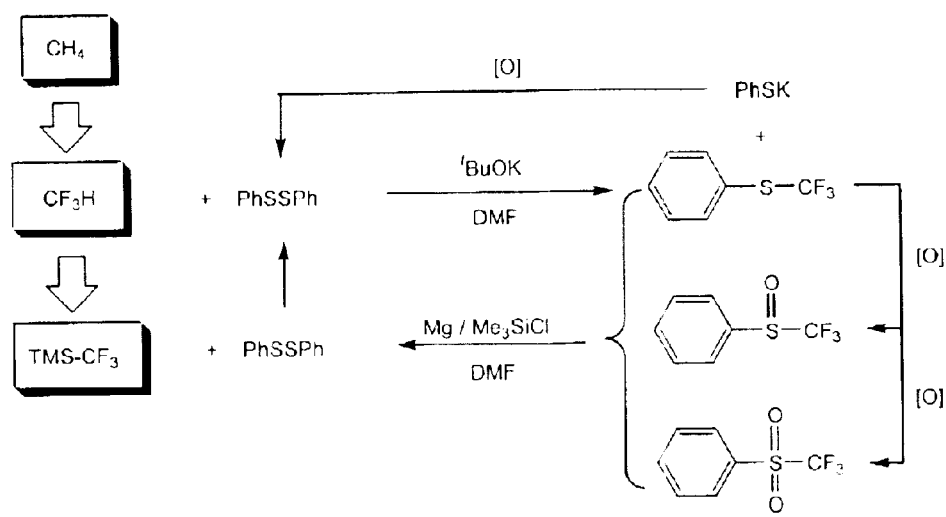

It is well known that the phenyl trifluoromethyl sulfone (1) and sulfoxide (2) can be readily prepared from trifluoromethane (manufactured from methane) and diphenyl disulfide (PhSSPh). Since in the present fluoroalkylation process, PhSSPh is produced as a reductive byproduct, the presently developed method provides a novel and useful "pseudo-catalytic" pathway for the production of (trifluoromethyl)silanes from readily available trifluoromethane and chlorosilanes, as illustrated in FIG. 5.

EXAMPLES

General: Unless otherwise mentioned, all reagents were purchased from commercial sources. Trifluoromethyl phenyl sulfone and sulfoxide were prepared from trifluoromethyl phenyl sulfide, which was obtained either from Aldrich or prepared from fluoroform and PhSSPh. Other known sulfides, sulfoxides and sulfones were prepared according to the reported procedures. Mg turnings were used without any special pretreatment. DMF was distilled over calcium hydride and stored over activated molecular sieves. All the reactions were carried out using Schlenk equipment, and the reactions were monitored by $^{19}F$ NMR periodically. $^1H$, $^{13}C$, $^{19}F$ and $^{29}Si$ NMR spectra were recorded on 500 and 360 MHz superconducting NMR spectrometers. $^1H$ NMR chemical shifts were determined relative to internal $(CH_3)_4Si$ (TMS) at δ0.0 or to the signal of a residual protonated solvent: $CDCl_3$ δ7.26. $^{13}C$ NMR chemical shifts were determined relative to internal TMS at δ0.0 or to the $^{13}C$ signal of solvent: $CDCl_3$ δ77.0. $^{19}F$ NMR chemical shifts were determined relative to internal $CFCl_3$ at δ0.0. $^{29}Si$ NMR chemical shifts were determined relative to internal TMS at δ0.0. IR spectra were obtained on a Perkin-Elmer 2000 FTIR Spectrometer. GC-MS were recorded on Hewlett Packard 5890 Gas Chromatograph with a Hewlett Packard 5971 Mass Selective Detector. High-resolution mass data of low boiling compounds were recorded on an Agilent 6890 GC chromatograph with micromass GCT (time of flight). Other high-resolution mass data were recorded on a VG 7070 high-resolution mass spectrometer.

Example 1

Preparation of (trifluoromethyl)trimethylsilane (14)

Into a 250 mL dry Schlenk flask under an argon atmosphere, was added 1.14 g Mg turnings (47.5 mmol) and 11.8 g TMSCl (109 mmol) in 50 mL DMF at 0° C. After stirring for 2 min, 4.62 g (23.8 mmol) of phenyl trifluoromethyl sulfoxide (2) in 5 mL DMF was added slowly via a syringe. The reaction mixture was stirred at 0° C. for 30 min, and then at room temperature for another 1.5 h until all the starting material was transformed into product 14 (monitored by $^{19}F$ NMR). All the low boiling fractions were collected under vacuum into a trap (cooled in liquid nitrogen), warmed to room temperature and then washed with ice water (50 mL×3). After quick drying over activated molecular sieves, the organic mixture was fractionally distilled using a 30-cm long column to give 2.73 g (81% yield) product 3a, b.p. 53–55° C. (lit. b.p. 55–55.5° C.). $^1$H NMR (360 MHz, CDCl$_3$): δ0.25 (s, 9H, CH$_3$). $^{13}$C NMR (90 MHz, CDCl$_3$): δ-5.3 (s, CH$_3$); 131.7 (q, $^1J_{C\text{-}F}$=321.8 Hz, CF$_3$). $^{19}$F NMR (338 MHz, CDCl$_3$): δ-67.2.

Similarly, compound 1 was used to prepare 14 in 82% isolated yield. Compound 3 also could be used to prepare 14, but the reaction was found to be sluggish.

Example 2

Preparation of (trifluoromethyl)triethylsilane (15)

Into a flame-dried Schlenk flask containing 1.03 g (43 mmol) magnesium turnings and 30 mL DMF under argon, was added 3.0 g (14 mmol) of trifluoromethyl phenyl sulfone (1) at 0° C. After stirring for 5 minutes, 6.45 g (43 mmol) triethylsilyl chloride was added dropwise via syringe. The color of the reaction mixture slowly turned yellow. The progress of the reaction was monitored by $^{19}$F NMR periodically. After 1 h, the mixture was slowly warmed to room temperature over 20 minutes period and the reaction mixture was washed with 50 mL ice water. After removing the excess Mg, the solution was extracted with pentane (30 mL×3). The pentane phase was washed carefully with cold 98% sulfuric acid (30 mL×4) to remove most of the siloxane and silanol. Subsequently, the organic phase was washed with cold water (30 mL×2), saturated aqueous NaHCO$_3$ solution (30 mL×2), water (20 mL×2) and dried over anhydrous magnesium sulfate. The solvent was removed under vacuum (~100 Torr), and the resulting crude product also contains PhSSPh as a byproduct (characterized by both GC-MS and NMR). The crude product was carefully purified by small scale fractional distillation to give 2.48 g (95% yield) (trifluoromethyl)triethylsilane (15), b.p.=56~58° C./60 Torr (lit. b.p. 52~54° C./10 Torr). GC-MS showed its purity was higher than 96%. $^1$H NMR (500 MHz, CDCl$_3$): δ0.79 (q, $^3J_{H\text{-}H}$=7.9 Hz, 6H); 1.04 (t, $^3J_{H\text{-}H}$=7.9 Hz, 9H). $^{13}$C NMR (125 MHz, CDCl$_3$): δ0.79 (s, CH$_2$); 6.37 (s, CH$_3$); 132.19 (q, $^1J_{C\text{-}F}$=323.5 Hz, CF$_3$). $^{19}$F NMR (470 MHz, CDCl$_3$): -61.30. $^{29}$Si NMR (99 MHz, CDCl$_3$): δ7.74 (q, $^2J_{Si\text{-}F}$=32.0 Hz). GC-MS (m/z): 184 (M$^+$), 155 (M-Et), 115(Et$_3$Si$^+$).

Example 3

Preparation of (trifluoromethyl)t-butyldimethylsilane (16)

Into a dry 250 mL Schlenk flask under an argon atmosphere, was added 5.14 g Mg turnings (214 mmol) and 32.3 g (214 mmol) t-butyldimethylsilyl chloride in 150 mL DMF at -30° C. Subsequently, 15.0 g (71.4 mmol) of 1 in 10 mL DMF was added slowly via a syringe. The reaction mixture was stirred at room temperature at -30° C. for 1 h, and then at room temperature for another 2 h until all the starting material was consumed ($^{19}$F NMR showed that the conversion was 75%). The reaction mixture was washed with ice water, followed by extraction with pentane (30 mL×4 ). Combined pentane phase was further washed carefully with cold 98% sulfuric acid (20 mL×4) to remove most of the siloxane and silanol. Then the pentane phase was washed with cold NaHCO$_3$ aqueous solution three times until pH paper indicated neutral pH. The pentane phase was dried over MgSO$_4$ and solvent evaporated to give a crude product that was fractionally distilled to give 7.46 g colorless liquid 16 (95° C./410 Torr), which turned to a transparent crystalline solid at room temperature (m.p. 52~54° C., sublimes), yield 57%. $^1$H NMR (500 MHz, CDCl$_3$): δ0.20 (s, 6H); 0.99 (s, 9H). $^{13}$C NMR (125 MHz, CDCl$_3$): δ-8.8; 16.0; 26.0; 132.0 (q, $^1J_{C\text{-}F}$=323.8 Hz, CF$_3$). $^{19}$F NMR (470 MHz, CDCl$_3$): δ-61.8. $^{29}$Si NMR (99 MHz, CDCl$_3$): δ8.4 (q, $^1J_{Si\text{-}F}$=32.8 Hz). GC-MS (m/z): 184 (M$^+$), 127 (M$^+$-$^t$Bu), 115 (M$^+$-CF$_3$), 99 (M$^+$-CF$_3$—CH$_3$), 57 (tBu$^+$). High-resolution GC-MS (EI): m/z calculated for C$_7$H$_{15}$F$_3$Si (M$^+$) 184.0895, found 184.0943.

Example 4

Preparation of tris(trimethylsilyl)trifluoromethylsilane (17)

Procedure was similar as above examples: Into 2 g (83 mmol) Mg turnings and 1 g (4.76 mmol) 1 in 20 mL DMF at -40° C., was slowly added 3 g (10.6 mmol) tris (trimethylsilyl)silyl chloride in 10 mL DMF. The reaction mixture was then stirred at -40° C. for 1 h and between -40° C.~-20° C. for another 2 h, until all of 1 were consumed (monitored by $^{19}$F NMR). The reaction mixture was washed with ice water, followed by extraction with pentane (20 mL×4). The pentane phase was washed with cold 98% sulfuric acid (10 mL×3) to remove most of the siloxane and silanol, washed with cold NaHCO$_3$ aqueous solution three times until pH paper indicated neutral pH. After drying over MgSO$_4$ and solvent removal, the crude product was further purified by silica gel chromatography (pentane as eluent) to give 0.93 g (62% yield) solid product 17 that sublimes at 50° C./10 Torr. $^1$H NMR (500 MHz, CDCl$_3$): δ0.26 (s, 27 H). $^{13}$C NMR (125 MHz, CDCl$_3$): δ0.5 (s, CH$_3$); 136.8 (q, $^1J_{C\text{-}F}$=328.0 Hz, CF$_3$). $^{19}$F NMR (470 MHz, CDCl$_3$): δ-41.4 $^{29}$Si NMR (99 MHz, CDCl$_3$): δ-66.8 (q, $^2J_{Si\text{-}F}$=27.5 Hz, 1 Si); -12.5 (q, $^3J_{Si\text{-}F}$=4.6 Hz, 3Si). GC-MS (m/z): 316 (M$^+$), 247 [(Me$_3$Si)$_3$Si$^+$], 69 (CF$_3{}^+$). High-resolution GC-MS (EI): m/z calculated for C$_{10}$H$_{27}$F$_3$Si$_4$ (M$^+$)316.1142, found 316.1110.

Example 5

Preparation of (difluoromethyl)trimethylsilane (18)

Into a mixture of 4.8 g (200 mmol) Mg turnings, 28.93 g (266 mmol) TMSCl and 100 mL DMF at 0° C., was added 12.80 g (66.7 mmol) difluoromethyl phenyl sulfone (4) in 10 mL DMF slowly. The reaction mixture was stirred at 0° C. for 90 min until $^{19}$F NMR showed that all the 4 was consumed. All the low boiling species was separated out by bulb to bulb distillation, followed by washing with ice water (30 mL×3) and drying over molecular sieve. Fractional distillation (using 30-cm long distillation column) afforded 4.96 g product 18, b.p. 52° C. (lit. b.p. 50° C.), yield 76%. $^1$H NMR (360 MHz, CDCl$_3$): δ0.15 (s, 9H); 5.82 (t, $^2J_{H\text{-}F}$=46.5 Hz, 1H). $^{13}$C NMR (90 MHz, CDCl$_3$): δ-5.4 (t, $^3J_{C\text{-}F}$=2.8 Hz); 123.9 (t, $^1J_{C\text{-}F}$=254.7 Hz). $^{19}$F NMR (338 MHz, CDCl$_3$): δ-140.1 (d, $^2J_{F\text{-}H}$=46.8 Hz).

Example 6

Preparation of (difluoromethyl)triethylsilane (19)

Into a mixture of 5 g (26 mmol) difluoromethyl phenyl sulfone (4), 1.9 g Mg turnings (78 mmol) and 150 mL DMF at -40° C., was slowly added 11.8 g (78 mmol) chlorotriethylsilane. The reaction mixture was then stirred at -40° C. to 10° C. during a 4 h period until $^{19}$F NMR indicated all of 4 was consumed. Similar work-up as above and fractional distillation gave 2.2 g product 19, b.p. 71° C./56 Torr, yield 51%. $^1$H NMR (500 MHz, CDCl$_3$): δ0.72 (q, $^3J_{H-H}$=8.0 Hz, 6H); 1.02 (t, $^3J_{H-H}$=8.0 Hz, 9H); 5.95 (t, $^2J_{H-F}$=46.0 Hz, 1H). $^{13}$C NMR (125 MHz, CDCl$_3$): δ0.6 (s, CH$_2$); 6.7 (s, CH$_3$); 124.3 (t, $^1J_{C-F}$=254.8 Hz). $^{19}$F NMR (470 MHz, CDCl$_3$): δ−137.6 (d, $^2J_{F-H}$=45.8 Hz). $^{29}$Si NMR (99 MHz, CDCl$_3$): δ3.3 (t, $^2J_{Si-F}$=24.8 Hz). GC-MS (m/z): 166 (M$^+$); 115 (Et$_3$Si$^+$); 51 (CF$_2$H$^+$).

Example 7

Preparation of 1,2-bis(trimethylsilyl)-1,1,2,2-tetrafluoroethane (20)

Into a mixture of 0.42 g (17.5 mmol) of Mg turnings, 1.92 g (17.7 mmol) of TMSCl and 10 mL DMF, was added 1.60 g (5.9 mmol) of bromodifluoromethyl phenyl sulfone (23). The reaction mixture was stirred at 0° C. for 30 min, and at room temperature for another 30 min until $^{19}$F NMR showed all of 23 was consumed (the yield of 20 was 76% and by-product TMSCF$_2$TMS, 18% by $^{19}$F NMR analysis). The reaction mixture was washed with ice water followed by extraction with pentane (10 mL×4). The pentane phase was washed with cold 98% sulfuric acid (10 mL×3) to remove most of the siloxane and silanol. Then the pentane solution was washed with cold NaHCO$_3$ aqueous solution three times until the pH paper indicated neutral pH. After drying over MgSO$_4$ and solvent removal, the crude product was further purified by fractional distillation and then recrystallization at −20° C. to give 0.40 g crystalline product 20, m.p. 40~42° C., yield 55%. $^1$H NMR (500 MHz, CDCl$_3$): δ0.24 (s, 18H). $^{13}$C NMR (125 MHz, CDCl$_3$): δ−4.0 (m, CH$_3$); 126.6 (tt, $^1J_{C-F}$=265.0 Hz; $^2J_{C-F}$=45.9 Hz). $^{19}$F NMR (470 MHz, CDCl$_3$): δ−122.3.

Compound 20 was also prepared by using PhSO$_2$CF$_2$O$_2$SPh or PhSO$_2$CF$_2$TMS as the starting material.

Example 8

Preparation of phenyl (trimethylsilyl)difluoromethyl sulfide (21)

Into a mixture of 0.22 g (9.2 mmol) Mg turnings, 1.99 g (18.3 mmol) of TMSCl and 20 ml DMF at room temperature, was added 1.1 g (4.6 mmol) bromodifluoromethyl phenyl sulfide (24). The reaction was stirred at room temperature for another 1 h. Excess TMSCl was removed under vacuum (~10 mmHg). The residue was washed with ice water and then extracted with dichloromethane (20 mL×3). The organic phase was further washed with brine and water successively, and dried over MgSO$_4$. After solvent removal, the crude product was further purified by silica gel chromatography (pentane as eluent) to give 905 mg (85% yield) product 21 as colorless liquid, b.p. 86~87° C./4 Torr. $^1$H NMR (500 MHz, CDCl$_3$): δ0.25 (s, 9H); 7.37 (m, 3H); 7.59 (d, 2H). $^{13}$C NMR (125 MHz, CDCl$_3$): δ−4.2; 126.3 (t, $^3J_{C-F}$=4.1 Hz); 128.8; 129.3; 134.0 (t, $^1J_{C-F}$=300.1 Hz); 136.2. $^{19}$F NMR (470 MHz, CDCl$_3$): δ−88.1 (s). $^{29}$Si NMR (99 MHz, CDCl$_3$): 7.7 (t, $^2J_{Si-F}$=31.28 Hz). IR (neat): 3064; 2965; 2904; 1884; 1585; 1475; 1441; 1414; 1307; 1255; 1076; 1025; 962; 884; 850; 825; 744; 703; 690; 631; 607; 496 cm$^{-1}$. GC-MS (m/z): 232 (M$^+$), 109 (PhS$^+$), 73 (Me$_3$Si$^+$). HRMS (DEI): m/z calculated for C$_{10}$H$_{14}$F$_2$SSi (M$^+$) 232.0553, found 232.0545.

Example 9

Preparation of phenyl(trimethylsilyl)difluoromethyl sulfone (22)

Phenyl(trimethylsilyl)-difluoromethyl sulfide (21) (2.0 g, 8.6 mmol) was oxidized with mCPBA (9.0 mmol) in 20 mL CH$_2$Cl$_2$ initially at 0° C., followed by stirring at room temperature overnight. After filtration, the filtrate was washed with Na$_2$SO$_3$ solution (10 mL×3), NaHCO$_3$ solution (10 mL×2) and water sequentially. After drying over MgSO$_4$ and solvent removal, the crude product was distilled to afford 1.2 g (51% yield) product 22 as a colorless liquid, b.p. 112~114° C./1 Torr. $^1$H NMR (500 MHz, CDCl$_3$): δ0.44 (s, 9H); 7.61 (t, 2H); 7.74 (t, 1H); 7.95 (d, 2H). $^{19}$F NMR (470 MHz, CDCl$_3$): δ−112.9. HRMS (DCI/NH$_3$): m/z calculated for C$_{10}$H$_{18}$F$_2$NO$_2$SSi (M+NH$_4$+) 282.0795, found 282.0787.

What is claimed is:

1. A method for preparing fluorinated alkyl silanes which comprises reacting a fluorinated alkyl sulfur containing compound with a silyl chloride in the presence of a reducing agent under reaction conditions sufficient to prepare a fluorinated alkyl silane.

2. The method of claim 1 wherein the reaction conditions include a temperature of between −50 and 30° C. and a time of between 10 minutes and 24 hours.

3. The method of claim 1 wherein the reaction conditions include a temperature of between 40 and 20° C. and a time of between 20 minutes and 6 hours.

4. The method of claim 1 wherein the reducing agent comprises a metal.

5. The method of claim 1 wherein reducing agent comprises magnesium or zinc metal.

6. The method of claim 1 specifically as:

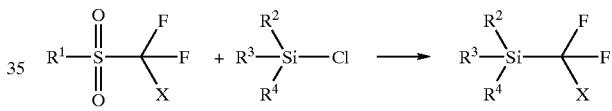

wherein

X is hydrogen or fluorine;

R$^1$ is an alkyl group of between 1 and 24 carbon atoms that is linear or branched or cyclic, single or fused rings, and are optionally substituted with one or more halogen, hydroxy, or alkoxy groups having 1 to eight carbon atoms, where the substituent does do not participate in the reaction, or an aryl group of between 6 and 24 members in a single ring or in fused rings, wherein the members are carbon or hetero atoms of nitrogen, oxygen or sulfur, and the ring(s) are optionally substituted with one to three substituents of an alkyl group having between 1 and 8 carbon atoms, a halogen, an alcohol, or an alkoxide of between 1 and 8 carbon atoms; and R$^2$, R$^3$ or R$^4$ independently is an alkyl group of between 1 and 24 carbon atoms that are linear or branched or cyclic, single or fused rings, and are optionally substituted with one or more halogen, hydroxy, or alkoxy groups having 1 to eight carbon atoms, where the substituent does do not participate in the reaction; or an aryl group of between 6 and 24 carbon atoms in a single ring or in fused rings, optionally substituted with one to three substituents of an alkyl group having between 1 and 8 carbon atoms, a halogen, an alcohol, or an alkoxide of between 1 and 8 carbon atoms.

7. The method of claim 1 specifically as:

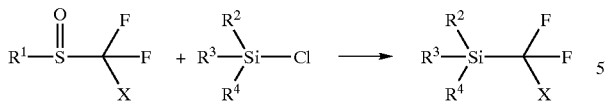

wherein

X is hydrogen or fluorine;

$R^1$ is an alkyl group of between 1 and 24 carbon atoms that is linear or branched or cyclic, single or fused rings, and are optionally substituted with one or more halogen, hydroxy, or alkoxy groups having 1 to eight carbon atoms, where the substituent does do not participate in the reaction, or an aryl group of between 6 and 24 carbon atoms in a single ring or in fused rings, optionally substituted with one to three substituents of an alkyl group having between 1 and 8 carbon atoms, a halogen, an alcohol, or an alkoxide of between 1 and 8 carbon atoms; and $R^2$, $R^3$ or $R^4$ independently is an alkyl group of between 1 and 24 carbon atoms that are linear or branched or cyclic, single or fused rings, and are optionally substituted with one or more halogen, hydroxy, or alkoxy groups having 1 to eight carbon atoms, where the substituent does do not participate in the reaction; or an aryl group of between 6 and 24 members in a single ring or in fused rings, wherein the members are carbon or hetero atoms of nitrogen, oxygen or sulfur, and the ring(s) are optionally substituted with one to three substituents of an alkyl group having between 1 and 8 carbon atoms, a halogen, an alcohol, or an alkoxide of between 1 and 8 carbon atoms.

8. The method of claim 1 specifically as:

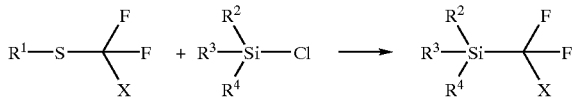

wherein

X is hydrogen or fluorine;

$R^1$ is an alkyl group of between 1 and 24 carbon atoms that is linear or branched or cyclic, single or fused rings, and are optionally substituted with one or more halogen, hydroxy, or alkoxy groups having 1 to eight carbon atoms, where the substituent does do not participate in the reaction, or an aryl group of between 6 and 24 carbon atoms in a single ring or in fused rings, optionally substituted with one to three substituents of an alkyl group having between 1 and 8 carbon atoms, a halogen, an alcohol, or an alkoxide of between 1 and 8 carbon atoms; and $R^2$, $R^3$ or $R^4$ independently is an alkyl group of between 1 and 24 carbon atoms that are linear or branched or cyclic, single or fused rings, and are optionally substituted with one or more halogen, hydroxy, or alkoxy groups having 1 to eight carbon atoms, where the substituent does do not participate in the reaction; or an aryl group of between 6 and 24 members in a single ring or in fused rings, wherein the members are carbon or hetero atoms of nitrogen, oxygen or sulfur, and the ring(s) are optionally substituted with one to three substituents of an alkyl group having between 1 and 8 carbon atoms, a halogen, an alcohol, or an alkoxide of between 1 and 8 carbon atoms.

9. The method of claim 1 wherein the reaction is carried out in the presence of a solvent.

10. The method of claim 9 wherein the solvent is dimethyl formamide, tetrahydrofuran, dimethyl sulfoxide, dioxane, dimethoxyethane, or tetrahydropyran.

11. The method of claim 1 wherein the fluorinated alkyl silane is subsequently used as a nucleophilic fluoromethylating agent.

12. The method of claim 1 wherein the fluorinated alkyl sulfur containing compound is a fluorinated alkyl sulfone, a fluorinated alkyl sulfoxide or a fluorinated alkyl sulfide.

13. The method of claim 12 wherein the fluorinated alkyl sulfone, fluorinated alkyl sulfoxide or fluorinated alkyl sulfide is phenyl trifluoromethyl sulfone, trifluoromethyl sulfoxide or trifluoromethyl sulfide, respectively.

14. The method of claim 12 wherein the fluorinated alkyl sulfur containing compound is phenyl trifluoromethyl sulfide which is prepared from trifluoromethane and diphenyl disulfide, thus providing an autocatalytic method.

* * * * *

UNITED STATES PATENT AND TRADEMARK OFFICE
CERTIFICATE OF CORRECTION

PATENT NO. : 6,803,477 B2
DATED : October 12, 2004
INVENTOR(S) : Prakash et al.

It is certified that error appears in the above-identified patent and that said Letters Patent is hereby corrected as shown below:

Column 12,
Line 24, before "and 20ºC. and a time", delete "40" and insert -- –40 --.
Lines 46 and 61, delete "does do not" and insert -- does not --.

Column 13,
Lines 14 and 25, delete "does do not" and insert -- does not --.

Column 14,
Lines 2 and 15, delete "does do not" and insert -- does not --.

Signed and Sealed this

Eighth Day of March, 2005

JON W. DUDAS
*Director of the United States Patent and Trademark Office*